US005484598A

United States Patent [19]

Schurig et al.

[11] Patent Number: 5,484,598

[45] Date of Patent: Jan. 16, 1996

[54] SOFT GELATIN MEDICAMENT CAPSULES WITH GRIPPING CONSTRUCTION

[75] Inventors: Gregory A. Schurig, Clearwater; Frank S. S. Morton, Seminole; Norman S. Stroud, Safety Harbor, all of Fla.

[73] Assignee: R.P. Scherer Corporation, Troy, Mich.

[21] Appl. No.: 313,423

[22] Filed: Sep. 27, 1994

Related U.S. Application Data

[63] Continuation of Ser. No. 164,629, Dec. 9, 1993, Pat. No. 5,380,534, which is a continuation of Ser. No. 931,593, Aug. 18, 1992, abandoned.

[51] Int. Cl.[6] ................................ A61K 6/00; A61K 7/00

[52] U.S. Cl. .......................... 424/401; 424/430; 424/436; 424/456

[58] Field of Search .............................. 128/272; 514/15, 514/16; 424/401, 78.03, 78.04, 456

[56] References Cited

U.S. PATENT DOCUMENTS

| | | | |
|---|---|---|---|
| 4,027,671 | 6/1977 | Sperti et al. | 128/272 |
| 4,659,696 | 4/1987 | Hirai et al. | 514/15 |
| 4,670,419 | 6/1987 | Uda et al. | 514/16 |
| 5,270,054 | 12/1993 | Bertolini | 424/401 |

*Primary Examiner*—Thurman K. Page
*Assistant Examiner*—William E. Benston, Jr.
*Attorney, Agent, or Firm*—Banner & Allegretti, Ltd.

[57] ABSTRACT

Knurled surfaces such as raised ribs are provided on the shell of a soft gelatin capsule in order to enhance gripping and manipulation of the capsule. The capsule has a removable tab at one end thereof which may also be provided with a knurled surface. One embodiment of the invention is a capsule used for delivery of medicaments to an external body surface. An alternative embodiment of the capsule is disclosed for insertion into a body orifice. The composition of the capsule includes a starch or starch derivative which gives the capsule a drier feel and increases the coefficient of friction of the surface of the shell, further improving the capsule's handling characteristics.

6 Claims, 2 Drawing Sheets

Fig. 1
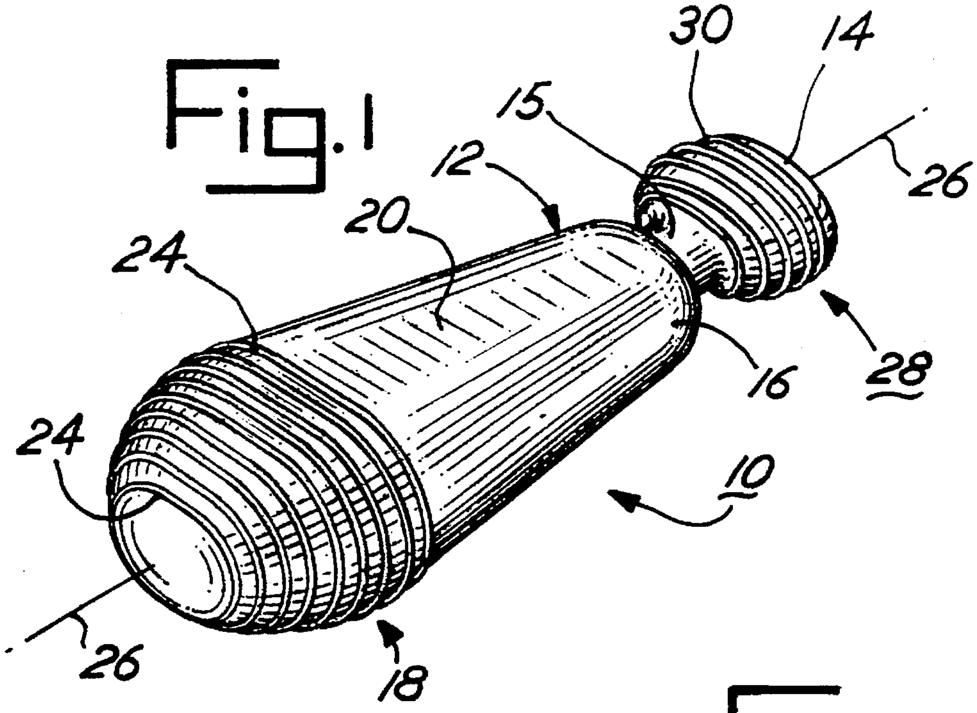
Fig. 2
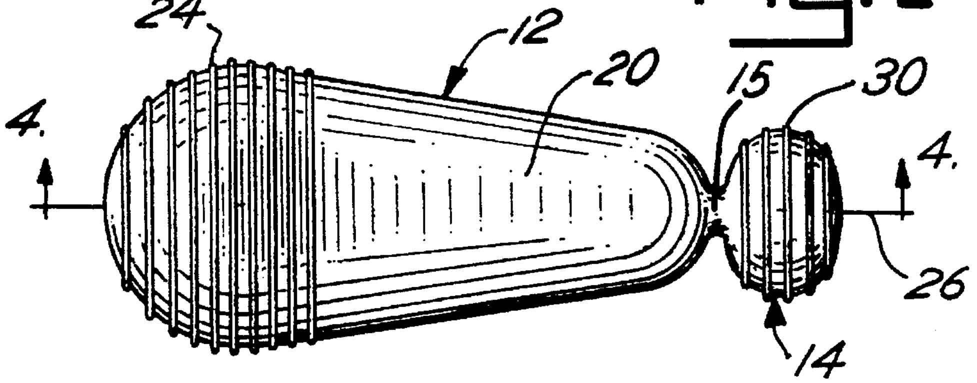
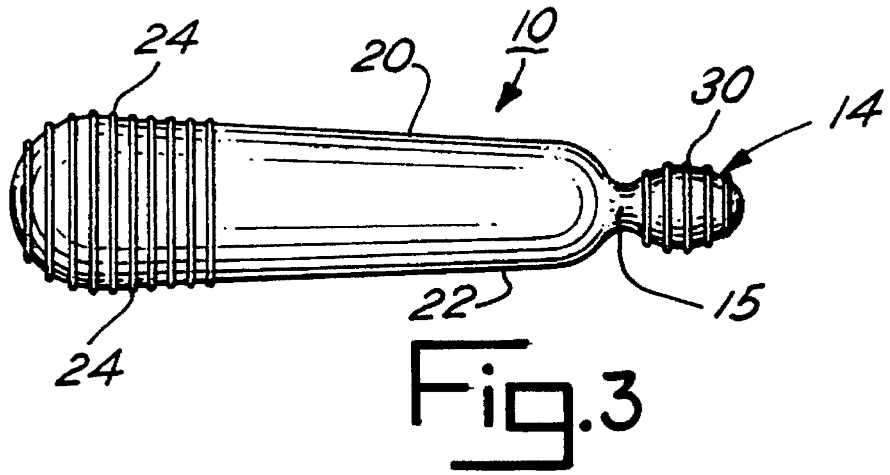
Fig. 3

Fig.4
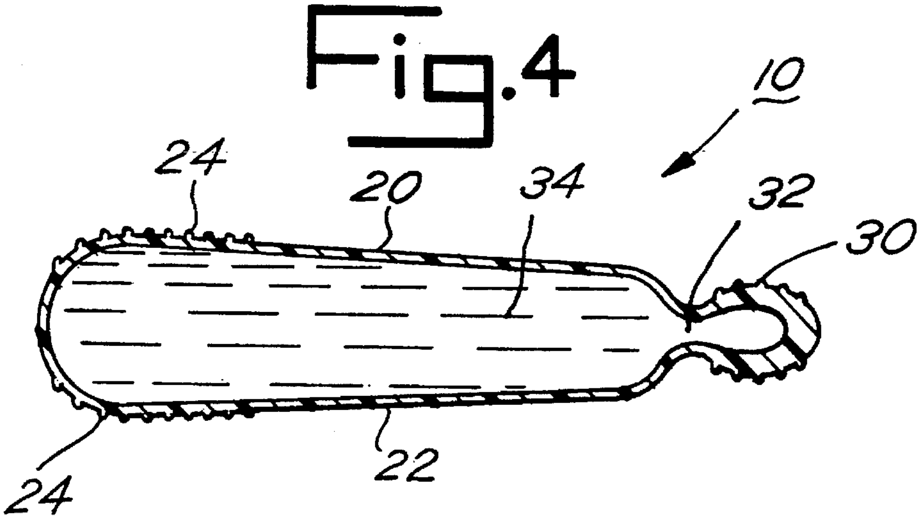
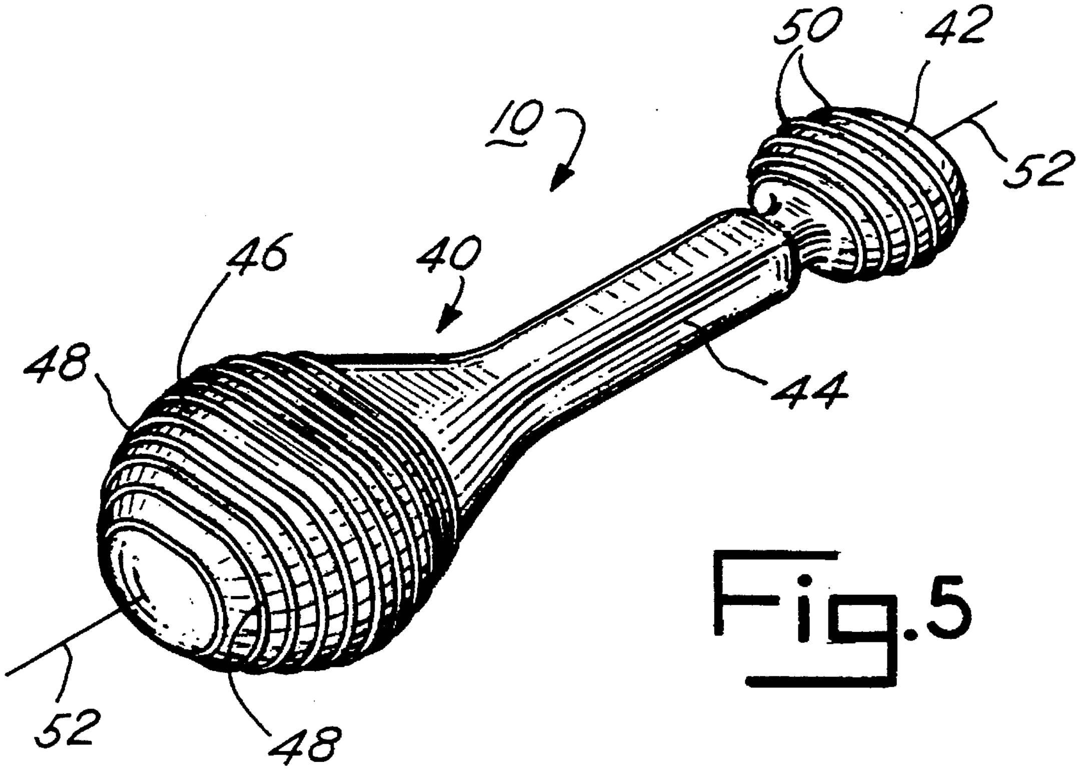
Fig.5

SOFT GELATIN MEDICAMENT CAPSULES WITH GRIPPING CONSTRUCTION

This is a continuation of application Ser. No. 08/164,629, U.S. Pat. No. 5,380,534, filed Dec. 9, 1993, which is a continuation of Ser. No. 07/931,593 filed Aug. 18, 1992, now abandoned.

BACKGROUND OF THE INVENTION

A. Field of the Invention

The present invention relates generally to disposable soft gelatin medicament capsules. More particularly, the present invention relates to a novel and advantageous gripping construction and composition for soft gelatin medicament capsules.

B. Background Art

Soft gelatin capsules are used for delivery of medicaments, including medicinal preparations, topical lotions, cosmetics and the like, to external body surfaces. Such capsules are also used for delivery of medicaments to tissues within body orifices. Delivery of the medicament, which is stored within the capsule, is accomplished by removing a portion of the capsule shell (typically by twisting or tearing off a tab), and then squeezing the capsule shell, thereby forcing the medicament from the capsule. Several patents disclosing representative soft gelatin capsules are U.S. Pat. No. 2,134,489 issued to Scherer, U.S. Pat. No. 2,334,600 issued to Boysen, U.S. Pat. No. 2,397,051 issued to Scherer, U.S. Pat. No. 4,278,633 issued to Fujii, and U.S. Pat. No. 5,063,057 issued to Spellman et al.

Soft gelatin capsules are often small in size since only a small quantity of medicament is stored therein. Furthermore, soft gelatin capsules are typically composed largely of gelatin or gelatinous materials. Such materials tend to have a smooth exterior surface with a low coefficient of static friction. Because of the capsule's small size and slippery surface, the user often has difficulty in performing the tasks required to complete the delivery of the medicament, that is, twisting or tearing off of the tab and compressing the capsule shell. This difficulty is even more compounded if the user's hands, or the capsule, are wet or oily, for example, due to bodily excretion or lubrication. Heretofore, a soft gelatin medicament capsule overcoming these difficulties has eluded the art.

SUMMARY OF THE INVENTION

A capsule is provided which comprises a hollow shell suitable for encapsulating a medicament. The shell has an exterior surface which is provided with a knurled texture region of sufficient area so as to enhance manipulation of the said capsule. The capsule further includes a removable tab integrally formed with the shell to seal the capsule. The medicament is expelled from the shell upon removal of the said tab and application of pressure to the shell. Since the shell, and preferably also the tab, have knurled surfaces, the difficulties of use associated with prior art capsules is largely eliminated.

In one embodiment of the invention, the shell is formed as an elongated body having top and bottom flattened portions, with the knurled texture region applied to both the top and bottom flattened portions. In an alternative embodiment of the invention, a capsule is provided which is suitable for insertion into an orifice, such as the rectum. In this alternative embodiment, the shell comprises an elongated neck portion and a bulb portion, with the knurled texture region applied to the bulb portion. In both embodiments, the removable tab may be provided with a knurled texture surface.

In yet another aspect of the invention, starch of starch derivatives are added to the base gelatin composition during manufacture. This addition increases the coefficient of friction on the exterior surface of the capsule shell and tab and thus further improve the ease of handling and manipulation of the capsule.

Accordingly, a principal object of the present invention is to provide a soft gelatin capsule which has improved gripping and handling characteristics to facilitate delivery of the encapsulated medicament to an exterior body surface.

A further object of the present invention to provide a soft gelatin capsule suitable for insertion into a body orifice which has improved gripping and handling characteristics, thereby facilitating medicament delivery to internal tissues.

Yet another object of the invention is provide a soft gelatin capsule which permits easier removal of the tab and expulsion of the medicament from the capsule.

Further objects, advantages, and features of the invention will become apparent from the following summary of the invention and detailed description of preferred embodiments.

BRIEF DESCRIPTION OF THE DRAWING

There is shown in the drawing presently preferred embodiments of the present invention, wherein like numerals in the various views refer to like elements and wherein:

FIG. 1 is a perspective view of a capsule according to the preferred embodiment of the present invention, showing a knurled texture applied to the shell and tab portions of the capsule to improve gripping and handling of the capsule;

FIG. 2 is a top view of the capsule of FIG. 1 showing the top flattened portion of the shell having a knurled texture applied to the exterior surface thereof;

FIG. 3 is a side elevational view of the capsule of FIGS. 1 and 2;

FIG. 4 is a cross-sectional view of the capsule of FIGS. 1–3; and

FIG. 5 is a perspective view of a capsule according to an alternative embodiment of the invention, showing a knurled texture applied to the bulb and tab portions to improve gripping and handling of the capsule.

DETAILED DESCRIPTION OF THE PREFERRED EMBODIMENTS

Referring now to FIGS. 1 through 3, a presently preferred embodiment of the invention is shown in perspective, top, and side elevational views, respectively. The embodiment of FIGS. 1–3 is particularly suitable for delivery of medicaments to an exterior bodily surface such as the skin. The embodiment of FIG. 5 is particularly suitable as a capsule for delivery of medicaments to tissues within a body orifice.

Referring now in particular to FIG. 1, the capsule 10 according to a preferred embodiment of the invention. The capsule 10 includes a hollow shell 12 which encapsulates the medicament, for example, a hemorrhoidal preparation. The capsule 10 further includes a removable tab 14 integrally formed with the shell 12 to seal the capsule 10. The tab 14 is removed by gripping the shell 12 and twisting off the tab 14. The tab 14 may be hollow or solid, though the neck portion 15 should be desirably hollow in order to permit the contents of the capsule to be in communication with the external environment after the tab 14 has been removed.

The shell 12 has an exterior surface 16, a portion of which is provided with a knurled texture region 18 to enhance the gripping and manipulation of the capsule 10. The knurled texture region 18 is chosen to be of sufficient surface area to increase the ease of handling the capsule 10 and the removal of the tab 14. With smaller size capsules, it may be preferable to apply a knurled texture to a larger percentage of the surface area of the shell 12 than is illustrated in FIGS 1–3.

In the embodiment of FIGS. 1–3, the shell 12 is shown as including top and bottom flattened portions 20 and 22. The flattened portions 20 and 22 provide a larger and flatter surface for the user's fingers than a rounded surface when pressure is applied to the shell 12 to force out the medicament. Of course, a capsule with the knurled texture region 18 can be provided without the flattened portions if desired.

The knurled texture region 18 of FIGS. 1–3 is shown as comprising a plurality of raised ribs 24 (slightly exaggerated in the figures) encircling the rear portion of the shell 12. Since both squeezing forces and forces along the central axis 26 in the direction of the tab 14 are required to expel the medicament from the capsule 10, it is preferable that the ribs 24 are applied to the exterior surface 16 of the shell 12 in a transverse orientation relative to the central axis 26. Since the thumb and forefinger are placed against the top and bottom flattened portions 20 and 22 during the squeezing of the shell 12, it is preferable to provide the knurled texture region on both the top and bottom portions 20 and 22.

The removable tab 14 of the capsule 10 is also shown as having a knurled texture region 28. The region 28 has a plurality of raised ribs 30 which facilitate the gripping of the tab 14 and the tearing or twisting of the tab 14 to open the capsule.

Raised rib structures, applied to exterior surface 16 of the shell 12, are the preferred gripping construction for the knurled texture region 18. The raised ribs 24 and 30 or other knurled texture is imparted to the gelatin ribbon prior to the manufacture and filling of the capsule.

Referring now to FIG. 4, the capsule 10 of FIGS. 1–3 is shown in vertical cross-section in a plane passing through the central axis 26 (FIG. 2). It can be seen from FIG. 4 that when the tab 14 is twisted or torn from the shell 12, an aperture 32 in the neck 15 is formed through which the medicament 34 is expelled from the capsule.

Referring now to FIG. 5, an alternative embodiment of the capsule 10 according to the present invention is shown in perspective view. The capsule 10 includes a shell 40 and a removable tab 42. The shell 40 includes a slender neck portion 44 and a bulb portion 46. Knurled textures, shown as raised ribs 48 and 50, are applied to the bulb portion 46 and tab 42, respectively. Once the tab 42 is removed from the neck portion 44 of the shell, the neck is ready for insertion into an orifice for delivery of the medicament to the tissue therein. In the embodiment of FIG. 5, the ribs 48 encircle the bulb portion 46 and are oriented transverse to the central axis 52 of the shell 40. As with the embodiment of FIGS. 1–4, the knurled texture regions of the bulb 46 and tab 42 enhance the gripping and manipulation of the capsule 10.

As noted previously, the exterior surface of gelatin capsules tends to be very smooth and slippery. However, the addition of a starch or starch derivative to the gelatin base during manufacture of the capsule has been found to produce drier, more tactile, and less slippery characteristics to the capsule surface. Capsules made with 0.1% to 30% by weight starch or starch derivatives, and preferably 5% to 20% by weight starch or starch derivatives, are suitable for this purpose. Suitable starch derivatives include high amylose starch, oxidized starch, esterified starch, acid-thinned starch, etherified starch, hydrolyzed starch, hydrolyzed and hydrogenated starch, and enzyme-treated starch. Another advantage of the addition of starch to the capsule wall is that it rigidifies the wall. This is particularly advantageous in the neck portion 15 of the capsule, since it facilitates the manipulation of the capsule and the ease of twist off at the tab 14.

Other polysaccharide thickening agents in the range of 0.1% to 15% and preferably in the range of 2% to 10% by weight, may be incorporated into the capsule composition to modify the surface of the capsule. Suitable thickeners include agar, acacia, alginates, carrageenans, gellan, guar, karaya, locust bean gum, pectin, pullulan, tragacanth, and xanthan.

Miscellaneous thickening agents in the range of 0.1% to 20%, and preferably 5% to 15% by weight, may be used. They include polyvinylpyrrolidone, polystyrene sulphonate, dextran sulphate, chitosan derivatives, cellulose, cellulose derivatives, bentonite and diatomaceous earths.

Miscellaneous gelatins in the amount of 0.1% to 50%, and preferably 5% to 40% by weight, may be incorporated into the capsule composition. They include hydrolysed gelatin, acylated gelatin and fish gelatin.

In addition, the plasticizer in the capsule shell may be modified by the use of one or more of the following materials, in the range of 2% to 40%, and preferably 5% to 30% by weight: partially dehydrated hydrogenated glucose syrups containing 1.4 sorbitans, polyglycerol, maltitol, and hydrogenated starch hydrolysate.

Preferable materials for the capsule 10 according to the present invention include high-amylose starch, starch, hydrolysed gelatin, maltitol and hydrogenated starch hydrolysate. A preferable composition for a dry (anhydrous) capsule shell 12 is:

| | |
|---|---|
| acylated gelatin | 49.6% by weight; |
| hydrolysed gelatin | 5.5% |
| high amylose starch | 4.8% |
| glycerol | 26.1% |
| hydrogenated starch hydrolysate | 14.0% |

Capsules according to the present invention may be made by conventional methods for producing soft gelatin capsules, e.g., the rotary die process, which are well known to those of skill in the art. The die used to form the capsules is dimply conformed to the desired capsule shape. The knurled or textured portion of the inventive capsule may be made according to the general methods disclosed in U.S. Pat. No. 5,246,635, which is incorporated herein by reference. In order to produce the knurled portions in the desired positions on the capsule, one or more texturing roller assemblies may be positioned relative to the gelatin ribbon to achieve the desired gripping construction(s). In order to produce a cross hatched pattern a plurality of texturing roller assemblies may be used at transverse angles relative to each other.

Use of the inventive capsules is also straightforward. The capsule is advantageously gripped by the knurled portion(s) while the tab is twisted or torn off, thus exposing the internal contents of the capsule to the exterior. The flexible capsule walls may then be squeezed, once again advantageously by the knurled region(s), to force out the contents of the capsule. In the case of medicaments to be applied to the exterior of the body, the contents may be squeezed onto the skin, for example. In the case of medicaments for internal applications, such as hemorrhoidal preparations, the elongated neck may be inserted into the bodily cavity or orifice of interest, such as the rectum, and the contents then squeezed into the orifice.

It will be appreciated that variations may be made to the preferred and alternative embodiments disclosed herein without departure from the true spirit and scope of the present invention. This true spirit and scope is defined by the appended claims, interpreted in light of the foregoing specification.

We claim:

1. An integral soft gelatin capsule applicator for containing a medicament in an unopened state and for expelling said medicament in an opened state, said integral capsule defining a longitudinal axis, comprising:

(a) a hollow flexible bulb portion extending substantially along said longitudinal axis including a first bulb end having an external bulb surface and a second tapered end, said first bulb end having a knurled texture extending substantially continuously about said external bulb surface, said knurled texture including outwardly extending projections to provide a frictional gripping surface for said first bulb end, said second tapered end defining a medicament expulsion port substantially remote from said first bulb end; and (b) a tab portion closing said medicament expulsion port in said unopened state and removable from said hollow flexible bulb portion by application of a twisting action substantially transverse to said longitudinal axis to provide said open state;

(c) said knurled texture substantially securing the user's fingers to grip said hollow flexible bulb portion without slippage permitting compressive forces to be applied to said hollow flexible bulb portion substantially perpendicular to said longitudinal axis to expel substantially all of said medicament from said capsule;

(d) said knurled texture of said first bulb end and said remoteness of said medicament expulsion port from said knurled texture cooperating to provide secure gripping of said first bulb end during normal compression thereof to expel said medicament through said medicament expulsion port and directing said medicament in a predetermined direction substantially away from said knurled texture, whereby said medicament is effectively and hygienically applied and spillage of said medicament onto said first bulb end is substantially avoided.

2. An integral capsule applicator as claimed in claim 1 wherein said second tapered end defines a neck portion, said neck portion having a neck length and a neck width, said neck width being substantially less than said neck length, said neck portion in said opened state adapted for insertion into a body orifice whereby said medicament is applied internally within said body orifice.

3. An integral capsule applicator as claimed in claim 2 wherein said outwardly projecting portions include a series of ribs extending outwardly from said external bulb surface in an orientation substantially transverse to said longitudinal axis.

4. An integral soft gelatin capsule applicator, said capsule defining a longitudinal axis, for containing a medicament in an unopened state and for applying said medicament in an opened state, comprising:

(a) a hollow flexible elongate body extending substantially along said longitudinal axis for encapsulating said medicament in said unopened state including a first bulb end having an external bulb surface, a middle portion, and a second tapered end, said middle portion tapering to said second tapered end, said first bulb end having a knurled texture extending substantially continuously about said external bulb surface, said knurled texture projecting outwardly from said external bulb surface to provide a frictional gripping surface for said first bulb end, said second tapered end defining a medicament expulsion port substantially remote from said first bulb end;

(b) said middle portion and said first bulb end of said capsule having flat top and bottom portions permitting secure gripping of said capsule;

(c) said flat top and bottom portions cooperating with said knurled texture to permit secure gripping said capsule without slippage of the user's fingers from said capsule so as to permit compressive forces to be applied to said middle portion and said first bulb end to expel substantially all of said medicament from said medicament expulsion port;

(d) a tab portion closing said medicament expulsion port and removable from said hollow flexible portion by application of a twisting action substantially transverse to said longitudinal axis to provide said open state.

5. An integral capsule applicator as claimed in claim 1 or claim 4 wherein said tab portion has an external tab surface and a knurled texture extending substantially continuously about said external tab surface and projecting outwardly therefrom to provide a frictional gripping surface to said tab portion, said knurled texture of said tab portion cooperating with said knurled texture applied to said first bulb end to permit secure gripping of said bulb portion and said tab portion during said twisting action to provide said open state.

6. An integral capsule applicator as claimed in claim 1 or claim 4, wherein said soft gelatin contains a starch or starch derivative in the amount of about 0.1% to about 30% by weight to provide a roughness to said integral capsule and said first bulb end thereof, said roughness assisting the secure gripping of said capsule.

* * * * *